(12) United States Patent
Boyd et al.

(10) Patent No.: US 6,288,289 B1
(45) Date of Patent: Sep. 11, 2001

(54) INTEGRATED EFFLUENT TREATMENT PROCESS FOR NITROAROMATIC MANUFACTURE

(75) Inventors: David Anthony Boyd, Vancouver; Stuart Alan Gairns, Burnaby; Alfred Alexander Guenkel, Vancouver, all of (CA)

(73) Assignee: Noram Engineering and Constructors Ltd., Vancouver (CA)

( * ) Notice: Subject to any disclaimer, the term of this patent is extended or adjusted under 35 U.S.C. 154(b) by 0 days.

(21) Appl. No.: 09/492,851

(22) Filed: Jan. 27, 2000

(51) Int. Cl.$^7$ .............................. C07C 205/00; C02F 1/68
(52) U.S. Cl. ..................... 568/934; 568/932; 210/761
(58) Field of Search ................................ 568/932, 934; 210/761

(56) References Cited

U.S. PATENT DOCUMENTS 4,338,199 * 7/1982 Modell ................................. 210/721
5,554,299 * 9/1996 Joulak et al. ......................... 210/712

OTHER PUBLICATIONS

Koo Chen, Hwahak Konghak, (1994), 32(3), 385–92.*

* cited by examiner

*Primary Examiner*—Sreeni Padmanabhan
*Assistant Examiner*—J. Parsa
(74) *Attorney, Agent, or Firm*—Breiner & Breiner, L.L.C.

(57) ABSTRACT

An integrated process for treating alkaline wash water effluent from nitroaromatic manufacture, principally containing nitro-hydroxy-aromatic compounds is described. The integrated process concentrates the alkaline wash water to recover chemicals and water prior to treating the concentrate through supercritical water oxidation. The supercritical water oxidation step consists of treating the concentrate in the presence of an oxygen source at conditions, which are supercritical for water to cause a substantial portion of the organic component of the concentrate to oxidize. The product effluent includes a gaseous component and a clean water component, and in the event that insoluble ash is formed, an ash component. The new integrated process results in reduced chemical and water consumption compared to existing processes. In addition, the treated wash water effluent can be recycled to process or directly discharged.

16 Claims, 5 Drawing Sheets

INTEGRATED EFFLUENT TREATMENT PROCESS FOR NITROAROMATIC MANUFACTURE

FIELD OF INVENTION

The present invention is directed to an integrated process for treating alkaline wash water effluent from nitroaromatic manufacture. The process concentrates alkaline wash water to recover chemicals and water prior to treating the concentrate through supercritical water oxidation. The new integrated process results in reduced chemical and water consumption compared to existing processes.

BACKGROUND OF INVENTION

Many industrially important aromatic nitrations, such as the production of nitrobenzene and dinitrotoluene, are commonly carried out in mixed acid, a nitrating solution of sulfuric acid and nitric acid. There are a number of different commercially practiced mixed acid nitrations. In the case of nitrobenzene manufacture, adiabatic nitration is commonly used (U.S. Pat. Nos. 4,091,042, 5,313,009, 5,763,697). Dinitrotoluene manufacture is carried out in concentrated mixed acid under isothermal and adiabatic conditions (U.S. Pat. Nos. 5,902,910, 5,689,018, 4,496,782).

Regardless of the type of aromatic or operating conditions, a key performance characteristic of mixed acid nitration processes is the amount and type of nitro-hydroxy-aromatic byproducts produced. For example, nitration of benzene produces nitrophenols, nitration of toluene produces nitroresols, and nitration of xylene produces nitroxylenols. The majority of nitrated aromatics are subsequently hydrogenated to their corresponding amine. It is common practice to remove nitro-hydroxy-aromatic byproducts from the nitroaromatic product, as these compounds are believed to adversely affect hydrogenation catalyst performance. Nitro-hydroxy-aromatic byproducts are commonly extracted from the crude nitroaromatic into alkaline wash water through counter-current washing. A number of different alkali chemicals are commonly used in washing, caustic soda and aqueous ammonia being the most common.

Treatment of the alkaline nitro-hydroxy-aromatic contaminated wash water, commonly called redwater due to its characteristic color, remains an active area of research and development. In the quantities and concentrations generated commercially, these compounds are toxic to most biological wastewater treatment systems. Due to its toxicity, nitration redwater is typically segregated from other plant effluents for separate treatment, usually in a chemical or thermal treatment process, leaving the majority of the nitration effluent relatively free of nitro-hydroxy-aromatic compounds. In order to reduce the quantity of contaminated effluent, and thus the cost of the special treatment required, alkaline wash water flow is commonly kept to the minimum required to achieve adequate product purity. Separation of inorganic compounds from the redwater is also important for some treatment technologies. For example, many sulfur compounds will produce sulfur dioxide upon incineration and, therefore, redwater should contain low levels of sulfate if it is to be incinerated.

No single redwater treatment technology has achieved widespread adoption by the nitration industry. The choice of a treatment technology is often dependent on local site conditions, economics and operator preference. The more common treatment techniques used commercially, and some previously disclosed processes for treatment of nitration redwater include:

Direct incineration of redwater. In this case, ammonia is commonly used as the alkali rather than caustic soda, since no ash is produced during combustion. However, incinerators can be unreliable due to high temperature operation and additionally have high operating costs due to the large amount of fuel required to first evaporate the redwater and then to raise it to combustion temperatures. Incineration is limited to ammonia washing since sodium or potassium hydroxide would react with carbon dioxide to form solid or molten carbonate salts in the incinerator. Incineration also often suffers from poor public image.

High-pressure, subcritical thermal-treatment. This technique includes wet air oxidation, pressurized thermal treatment without addition of an oxidant (U.S. Pat. No. 4,230,567), and thermal treatment with the addition of an oxidant such as nitric acid (U.S. Pat. No. 5,232,605) or oxygen (U.S. Pat. No. 5,250,193). These processes are effective at detoxification of redwater, but, due to the formation of stable intermediates such as carboxylic acids, further biological treatment is commonly required before release to a receiving water. These processes typically embody large, high-pressure reactors under exothermic conditions, posing some safety concerns.

High temperature, alkaline digestion of redwater. U.S. Pat. No. 5,221,440 describes an alkaline digestion process whereby nitro-hydroxy-aromatic compounds are converted to less toxic, oxalic acid-like compounds. The resulting effluent must then be neutralized and biologically treated before discharge.

Biological treatment. By blending the redwater with another much larger wastewater stream, the nitro-hydroxy-aromatic toxicity can be reduced to non-toxic levels. However, there remains the possibility of toxic shock to the biological system if nitro-hydroxy-aromatic concentrations are too high. In addition, biological removal efficiencies can be too low to meet discharge standards and commonly require the use of activated carbon or another secondary treatment method.

Acid precipitation, extraction and incineration. Nitro-hydroxy-aromatic compounds, such as nitrophenols or nitrocresols, can be precipitated under acidic conditions. The precipitates can be extracted from the aqueous phase into an organic phase for subsequent incineration (U.S. Pat. Nos. 4,597,567 and 4,925,565). Although these processes allow incineration of a concentrated nitro-hydroxy-aromatic solution, thereby reducing fuel costs, these processes still suffer from incinerator permitting issues. Even after the multiple unit operations of acidification, precipitation, extraction, concentration and incineration, the redwater extract typically requires further treatment to meet discharge standards.

Chemical oxidation. Redwater treatment processes using ozone, hydrogen peroxide/fentons reagent (U.S. Pat. No. 4,604,214) and iron/hydrochloric acid (U.S. Pat. No. 4,708,806) are known. Achieving required discharge standards with these processes without further processing is difficult and chemical reagent costs are high.

Activated carbon. Treatment of industrial scale redwater waste with activated carbon is technically feasible, but is prohibitively expensive.

Deep well injection. Some facilities dispose of redwater through deep disposal wells. This is not acceptable practice in most jurisdictions and does not reduce the toxicity of the effluent.

It is clear, therefore, that there remains a need for an effective redwater treatment process, especially for nitration production facilities that do not have access to a biological treatment plant. In addition, currently practiced redwater treatment technologies are not integrated into the nitroaromatic washing process. Integration provides the opportunity to recover and recycle water, product and chemicals.

SUMMARY OF INVENTION

The present invention relates to an integrated process to treat alkaline wash water effluent from nitroaromatic manufacture, for example nitrobenzene, nitrotoluene or nitroxylene, wherein the nitrated aromatic is produced in a reaction media of sulfuric acid, nitric acid and water. Mono-, di- and tri-nitrated nitroaromatic compounds are all commonly produced by such processes. The process integrates alkaline washing, commonly performed to remove nitro-hydroxy-aromatic compounds from the crude nitroaromatic stream, with an effluent concentrator and supercritical water oxidation treatment. The process includes an acidic contacting or extraction stage to remove mineral acids prior to the alkaline washing stage.

More specifically, alkaline wash water, containing nitro-hydroxy-aromatic compounds, free alkali and dissolved nitroaromatic, is concentrated in an effluent concentrator, whereby water and nitroaromatic product are recovered and recycled. When ammonia is used as the alkali source in nitroaromatic washing, the bulk of the free ammonia is recovered and reused in washing. The effluent concentrate, containing elevated concentrations of nitro-hydroxy-aromatic compounds, is then treated in the presence of an oxygen source at conditions supercritical for water, these conditions hereinafter at times referred to as "supercritical water oxidation." The resultant effluent includes a gaseous component and an aqueous component. A solid or insoluble ash can also be formed, as an ash component. Supercritical water oxidation can achieve such high nitro-hydroxy-aromatic destruction and total organic carbon (TOC) reduction, without NOx formation, that the resultant effluent can in many cases be discharged without further treatment. Alternatively, the resultant aqueous effluent can be recycled to the nitroaromatic process to further reduce water and alkali consumption.

The invention has many advantages. For example, water and chemical consumption in nitroaromatic washing are significantly reduced. In the case where ammonia is used, recovery allows increased ammonia concentrations to be used in the alkaline washing, improving nitro-hydroxy-aromatic extraction efficiency. In addition, treatment of the nitro-hydroxy-aromatic contaminated effluent through supercritical water oxidation, produces a very clean aqueous effluent stream suitable for direct discharge or recycle.

In comparison with ammonia washing and subsequent incineration of the contaminated effluent, the process offers the advantage of substantially lower energy consumption and much lower levels of NOx emissions. It is also believed that the new process will be more easily granted environmental permits, relative to incineration, and enjoy improved public and regulatory agency perception. A further advantage is that aqueous effluent discharge is reduced compared with known treatment methods considered hereinbefore.

TABLE 1

Figure 1:
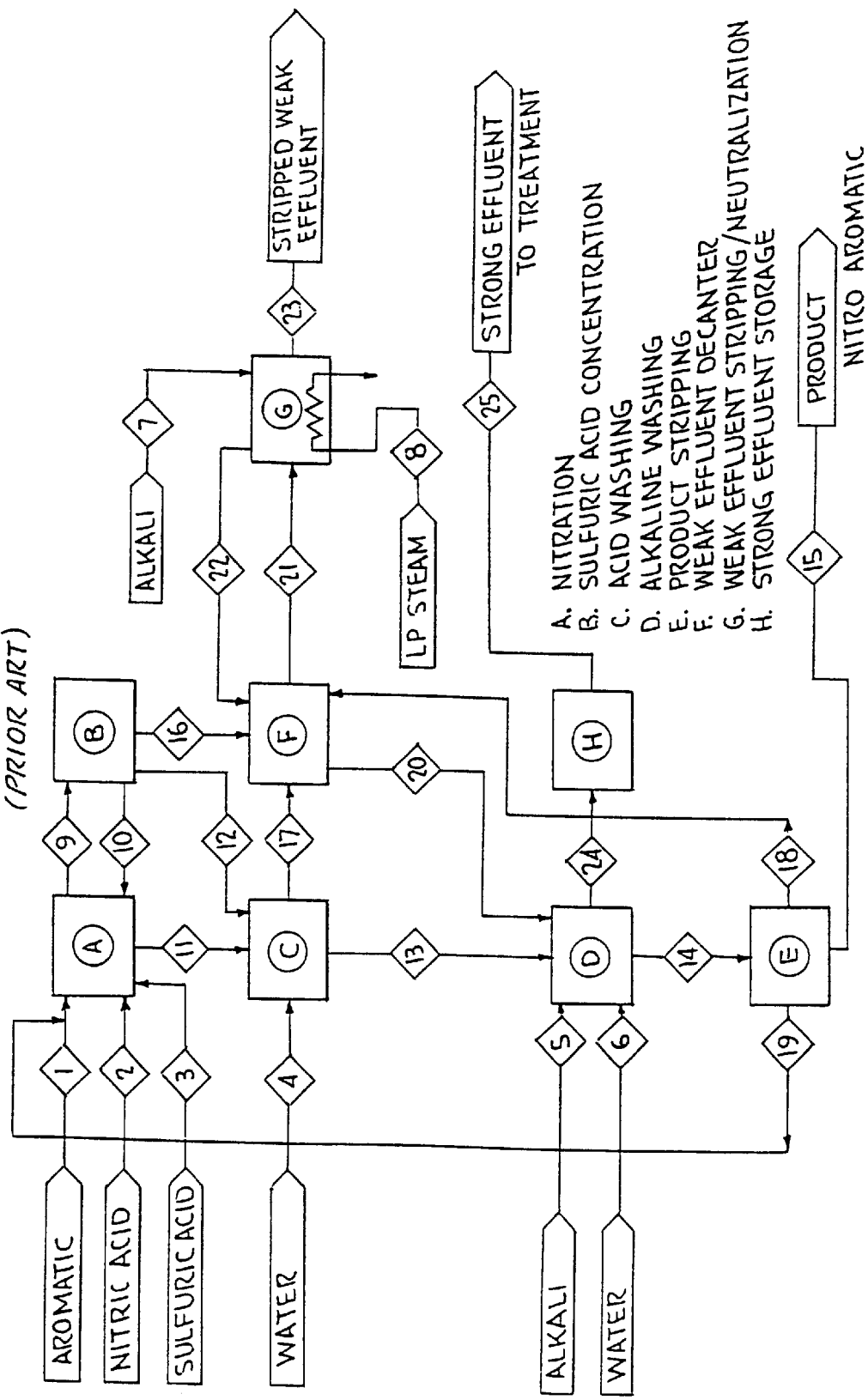
FIG. 1 is a schematic representation of the processing stages of commonly practiced nitroaromatic manufacture. Table 1 contains the stream flow data for the case of mononitrobenzene (MNB) manufacture with sodium hydroxide (caustic soda) as the alkali source in washing.

Stream Table for FIG. 1 (Case of MNB manufacture with caustic washing)

| Stream Number | | 1 | 2 | 3 | 4 | 5 | 6 | 7 | 8 | 9 | 10 | 11 | 12 | 13 |
|---|---|---|---|---|---|---|---|---|---|---|---|---|---|---|
| Total Flow | kg/h | 31,750.2 | 40,122.2 | 93.8 | 5,000.0 | 154.1 | 7,500.0 | 495.9 | 1,900.0 | 860,861 | 831.429 | 44,434.4 | 7,686.6 | 52,104.6 |
| Benzene | kg/h | 31,750.2 | | | | | | | | 225 | | 1,677.4 | 225.0 | 1,902.4 |
| Mononitro-benzene | kg/h | | | | | | | | | 7,500 | | 42,500.0 | 7,456.6 | 49,946.6 |
| Nitrophenols | kg/h | | | | | | | | | 5 | | 95.0 | 5.0 | 100.0 |
| Water | kg/h | | 14,444.0 | 3.8 | 5,000.0 | 131.0 | 7,500.0 | 421.5 | 1,900.0 | 271,122 | 249,429 | 81.0 | | 155.5 |
| Sulfuric Acid | kg/h | | | 90.0 | | | | | | 582,009 | 582,000 | 81.0 | | |
| Nitric Acid | kg/h | | 25,678.2 | | | | | | | | | | | |
| Sodium Hydroxide | kg/h | | | | | 23.1 | | 74.4 | | | | | | |
| Sodium Sulfate | kg/h | | | | | | | | | | | | | |
| Sodium Nitrophenolates | kg/h | | | | | | | | | | | | | |

TABLE 1-continued

Stream Table for FIG. 1 (Case of MNB manufacture with caustic washing)

| Stream Number | | 14 | 15 | 16 | 17 | 18 | 19 | 20 | 21 | 22 | 23 | 24 | 25 |
|---|---|---|---|---|---|---|---|---|---|---|---|---|---|
| Total Flow | kg/h | 52,035.5 | 49,978.0 | 21,746.0 | 5,016.5 | 155.5 | 1,901.9 | 53.4 | 28,279.5 | 1,414.8 | 27,360.5 | 7,776.6 | 7,776.6 |
| Benzene | kg/h | 1,902.4 | 0.5 | | | | 1,901.9 | | | | | | |
| Mononitrobenzene | kg/h | 49,977.5 | 49,977.5 | 43.4 | 10.0 | | | 53.4 | 53.4 | 53.4 | | 22.5 | 22.5 |
| Nitrophenols | kg/h | | | | | | | | | | | | |
| Water | kg/h | 155.5 | | 21,693.6 | 4,925.5 | 155.5 | | | 28,136.1 | 1,361.5 | 27,229.2 | 7,640.7 | 7,640.7 |
| Sulfuric Acid | kg/h | | | 9.0 | 81.0 | | | | 90.0 | | | | |
| Nitric Acid | kg/h | | | | | | | | | | | | |
| Sodium Hydroxide | kg/h | | | | | | | | | | | 1.1 | 1.1 |
| Sodium Sulfate | kg/h | | | | | | | | | | 131.3 | | |
| Sodium Nitrophenolates | kg/h | | | | | | | | | | | 112.2 | 112.2 |

TABLE 2

Figure 2:
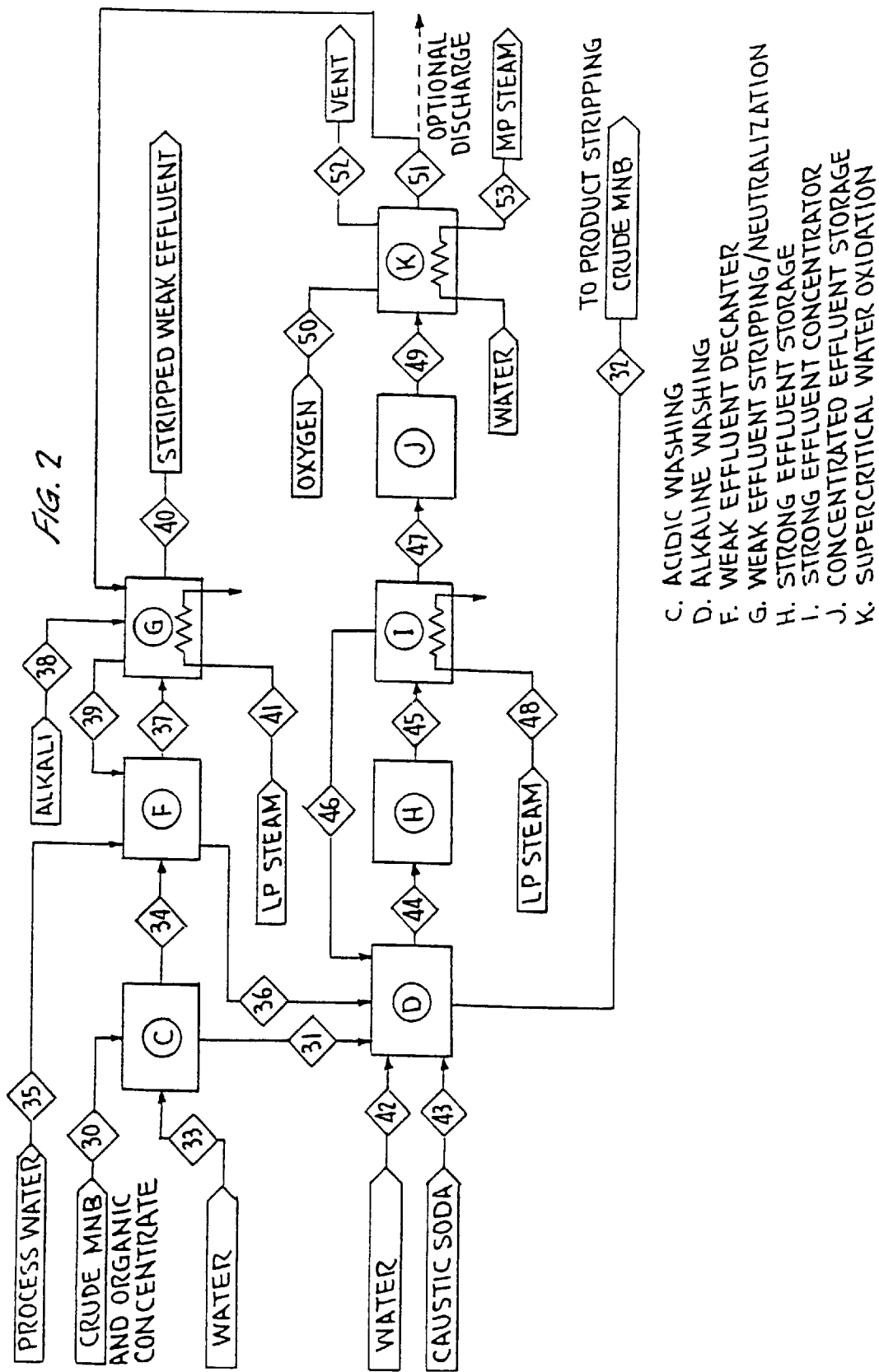
FIG. 2 is a schematic representation of the invention for MNB manufacture, wherein sodium hydroxide is used as the alkali source in the alkaline washing step. The alkali value in the effluent from the supercritical water oxidation is used to neutralize the weak effluent. Table 2 contains the stream flow data.

Stream Table for FIG. 2 (Invention with caustic MNB washing plant)

| Stream Number | | 30 | 31 | 32 | 33 | 34 | 35 | 36 | 37 | 38 | 39 | 40 | 41 |
|---|---|---|---|---|---|---|---|---|---|---|---|---|---|
| Total Flow | kg/h | 52,121.1 | 52,104.6 | 52,057.5 | 5,000.0 | 5,016.5 | 21,901.5 | 53.4 | 28,343.0 | 341.8 | 1,478.4 | 28,643.3 | 2,000.0 |
| Benzene | kg/h | 1,902.4 | 1,902.4 | 1,902.4 | | | | | | | | | |
| Mononitrobenzene | kg/h | 49,956.6 | 49,946.6 | 49,999.5 | | 10.0 | 43.4 | 53.4 | 53.4 | | 53.4 | | |
| Nitrophenols | kg/h | 100.0 | 100.0 | | | | | | | | | | |
| Water | kg/h | 81.0 | 155.5 | 155.5 | 5,000.0 | 4,925.5 | 21,849.2 | | 28,199.6 | 290.6 | 1,425.0 | 28,499.4 | 2,000.0 |
| Sulfuric Acid | kg/h | 81.0 | | | | 81.0 | 9.0 | | 90.0 | | | | |
| Nitric Acid | kg/h | | | | | | | | | | | | |
| Sodium Hydroxide | kg/h | | | | | | | | | 51.3 | | | |
| Sodium Sulfate | kg/h | | | | | | | | | | | 131.3 | |
| Sodium Nitrophenolates | kg/h | | | | | | | | | | | | |
| Sodium Carbonate | kg/h | | | | | | | | | | | | |
| Oxygen | kg/h | | | | | | | | | | | | |
| Nitrogen | kg/h | | | | | | | | | | | | |
| Carbon Dioxide | kg/h | | | | | | | | | | | 12.6 | |

| Stream Number | | 42 | 43 | 44 | 45 | 46 | 47 | 48 | 49 | 50 | 51 | 52 | 53 |
|---|---|---|---|---|---|---|---|---|---|---|---|---|---|
| Total Flow | kg/h | 1,243.4 | 154.1 | 7,542.6 | 7,542.6 | 6,044.6 | 1,498.0 | 6,300.0 | 1,498.0 | 98.9 | 1,421.5 | 175.4 | 290.0 |
| Benzene | kg/h | | | | | | | | | | | | |
| Mononitrobenzene | kg/h | | | 22.2 | 22.2 | 21.7 | 0.5 | | 0.5 | | | | |
| Nitrophenols | kg/h | | | | | | | | | | | | |
| Water | kg/h | 1,243.4 | 131.0 | 7,406.5 | 7,406.5 | 6,022.4 | 1,384.1 | 6,300.0 | 1,384.1 | | 1,390.9 | 8.3 | 290.0 |
| Sulfuric Acid | kg/h | | | | | | | | | | | | |
| Nitric Acid | kg/h | | | | | | | | | | | | |
| Sodium Hydroxide | kg/h | | 23.1 | 1.1 | 1.1 | | 1.1 | | 1.1 | | | | |
| Sodium Sulfate | kg/h | | | | | | | | | | | | |
| Sodium Nitrophenolates | kg/h | | | 112.8 | 112.8 | 0.6 | 112.2 | | 112.2 | | | | |
| Sodium Carbonate | kg/h | | | | | | | | | | 30.5 | | |
| Oxygen | kg/h | | | | | | | | | 98.9 | | 19.8 | |
| Nitrogen | kg/h | | | | | | | | | | | 15.3 | |
| Carbon Dioxide | kg/h | | | | | | | | | | | 132.0 | |

TABLE 3

Figure 3:
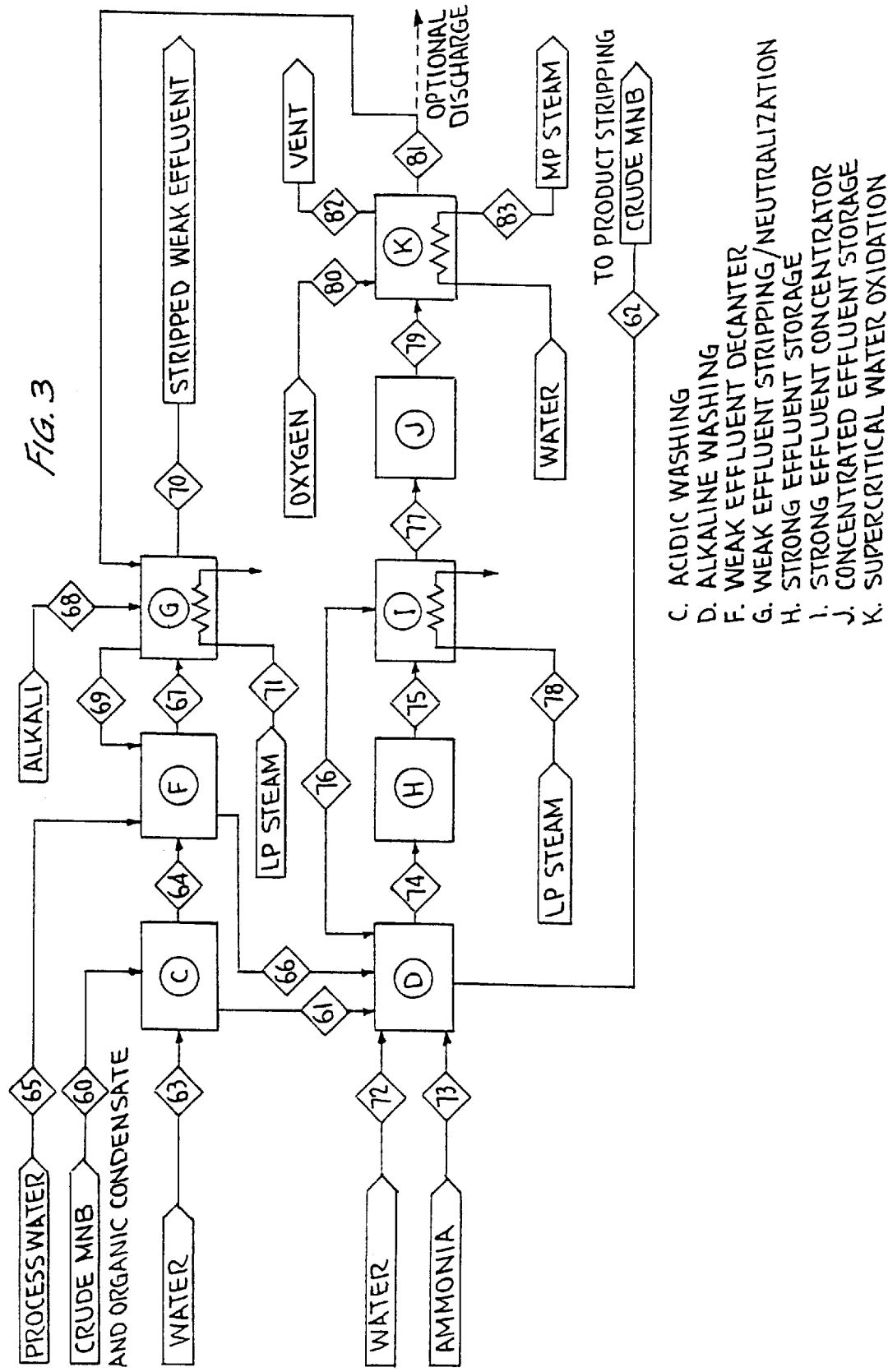
FIG. 3 is a schematic representation of the invention for MNB manufacture, wherein ammonia solution is used as the alkali source in the alkaline washing step. Weak ammonia solution is recovered and recycled back to alkaline washing. Table 3 contains the stream flow data.

Stream Table for FIG. 3 (Invention with ammonia-based MNB washing plant)

| Stream Number | | 60 | 61 | 62 | 63 | 64 | 65 | 66 | 67 | 68 | 69 | 70 | 71 |
|---|---|---|---|---|---|---|---|---|---|---|---|---|---|
| Total Flow | kg/h | 52,121.1 | 52,104.6 | 52,058.3 | 5,000.0 | 5,016.5 | 21,901.5 | 53.4 | 28,256.7 | 495.9 | 1,392.1 | 29,368.8 | 2,000.0 |
| Benzene | kg/h | 1,902.4 | 1,902.4 | 1,902.4 | | | | | | | | | |
| Mononitrobenzene | kg/h | 49,956.6 | 49,946.6 | 49,999.3 | | 10.0 | 43.4 | 53.4 | 53.4 | | 53.4 | | |

TABLE 3-continued

Stream Table for FIG. 3 (Invention with ammonia-based MNB washing plant)

| | | | | | | | | | | | | | |
|---|---|---|---|---|---|---|---|---|---|---|---|---|---|
| Nitrophenols | kg/h | 100.0 | 100.0 | 1.0 | | | | | | | | | |
| Water | kg/h | 81.0 | 155.5 | 155.5 | 5,000.0 | 4,925.5 | 21,849.2 | | 28,113.3 | 421.5 | 1,338.7 | 29,215.8 | 2,000.0 |
| Sulfuric Acid | kg/h | 81.0 | | | | 81.0 | 9.0 | | 90.0 | | | | |
| Nitric Acid | kg/h | | | | | | | | | | | | |
| Sodium Hydroxide | kg/h | | | | | | | | | 74.4 | | | |
| Sodium Sulfate | kg/h | | | | | | | | | | | 131.3 | |
| Ammonia | kg/h | | | | | | | | | | | | |
| Ammonium Nitrophenolate | kg/h | | | | | | | | | | | 21.6 | |
| Ammonium Bicarbonate | | | | | | | | | | | | | |
| Oxygen | kg/h | | | | | | | | | | | | |
| Nitrogen | kg/h | | | | | | | | | | | | |
| Carbon Dioxide | kg/h | | | | | | | | | | | | |

| Stream Number | | 72 | 73 | 74 | 75 | 76 | 77 | 78 | 79 | 80 | 81 | 82 | 83 |
|---|---|---|---|---|---|---|---|---|---|---|---|---|---|
| Total Flow | kg/h | 1,947.4 | 34.5 | 7,430.8 | 7,430.8 | 5,349.1 | 2,081.7 | 5,500.0 | 2,008.2 | 108.4 | 2,008.2 | 181.8 | 290.0 |
| Benzene | kg/h | | | | | | | | | | | | |
| Mononitrobenzene | kg/h | | | 28.9 | 28.9 | 28.2 | 0.7 | | 0.7 | | | | |
| Nitrophenols | kg/h | | | | | | | | | | | | |
| Water | kg/h | 1,947.4 | 24.1 | 7,233.0 | 7,233.0 | 5,261.4 | 1,971.6 | 5,500.0 | 1,971.6 | | 1,986.6 | 8.8 | 290.0 |
| Sulfuric Acid | kg/h | | | | | | | | | | | | |
| Nitric Acid | kg/h | | | | | | | | | | | | |
| Sodium Hydroxide | kg/h | | | | | | | | | | | | |
| Sodium Sulfate | kg/h | | | | | | | | | | | | |
| Ammonia | kg/h | | 10.3 | 58.7 | 58.7 | 57.5 | 1.2 | | 1.2 | | | | |
| Ammonium Nitrophenolates | kg/h | | | 110.1 | 110.1 | 2.0 | 108.1 | | 108.1 | | | | |
| Ammonium Bicarbonate | kg/h | | | | | | | | | | 21.6 | | |
| Oxygen | kg/h | | | | | | | | | 108.4 | | 21.7 | |
| Nitrogen | kg/h | | | | | | | | | | | 19.8 | |
| Carbon Dioxide | kg/h | | | | | | | | | | | 131.5 | |

TABLE 4

Figure 4:
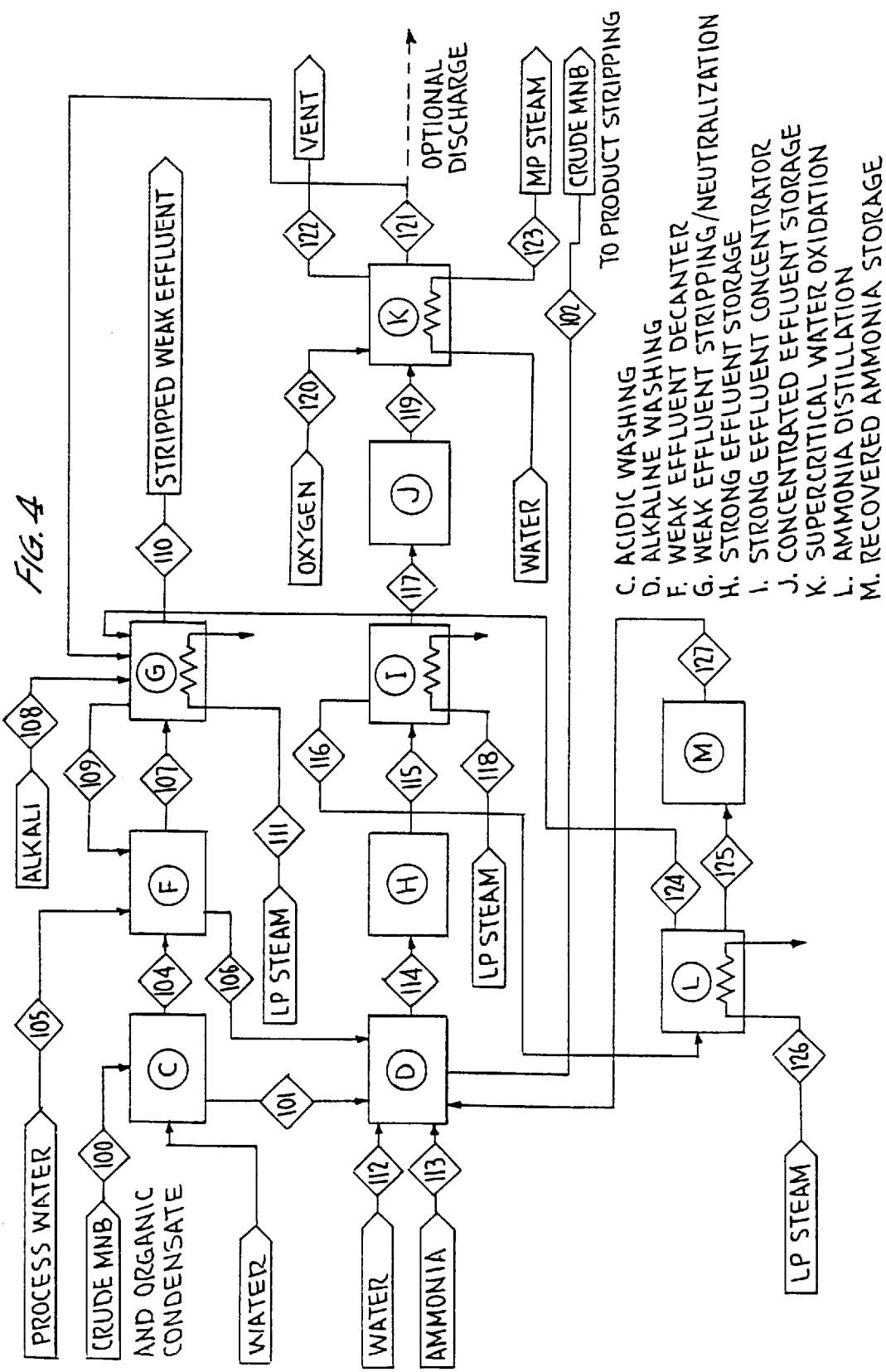
FIG. 4 is a schematic representation of the invention for MNB manufacture, wherein ammonia solution is used as the alkali source in the alkaline washing step, and ammonia distillation is included to increase the concentration of the ammonia recycled to alkaline washing. Table 4 contains the stream flow data.

Stream Table for FIG. 4 (Invention with ammonia-based MNB washing plant and ammonia concentration)

| Stream Number | | 100 | 101 | 102 | 103 | 104 | 105 | 106 | 107 | 108 |
|---|---|---|---|---|---|---|---|---|---|---|
| Total Flow | kg/h | 52,121.1 | 52,104.6 | 52,058.3 | 5,000.0 | 5,016.5 | 21,901.5 | 54.8 | 28,256.7 | 495.9 |
| Benzene | kg/h | 1,902.4 | 1,902.4 | 1,902.4 | | | | | | |
| Mononitrobenzene | kg/h | 49,956.6 | 49,946.6 | 49,999.3 | | 10.0 | 43.4 | 54.8 | 53.4 | |
| Nitrophenols | kg/h | 100.0 | 100.0 | 1.0 | | | | | | |
| Water | kg/h | 81.0 | 155.5 | 155.5 | 5,000.0 | 4,925.5 | 21,849.2 | | 28,113.3 | 421.5 |
| Sulfuric Acid | kg/h | 81.0 | | | | 81.0 | 9.0 | | 90.0 | |
| Nitric Acid | kg/h | | | | | | | | | |
| Sodium Hydroxide | kg/h | | | | | | | | | 74.4 |
| Sodium Sulfate | kg/h | | | | | | | | | |
| Ammonia | kg/h | | | | | | | | | |
| Ammonium Nitrophenolates | kg/h | | | | | | | | | |
| Ammonium Bicarbonate | kg/h | | | | | | | | | |
| Oxygen | kg/h | | | | | | | | | |
| Nitrogen | kg/h | | | | | | | | | |
| Carbon Dioxide | kg/h | | | | | | | | | |

| Stream Number | | 109 | 110 | 111 | 112 | 113 | 114 | 115 | 116 | 117 |
|---|---|---|---|---|---|---|---|---|---|---|
| Total Flow | kg/h | 1,393.5 | 34,198.8 | 1,900.0 | 6,766.8 | 43.8 | 7,295.9 | 7,295.9 | 5,252.7 | 2,043.2 |
| Benzene | kg/h | | | | | | | | | |
| Mononitrobenzene | kg/h | 54.8 | | | | | 28.4 | 28.4 | 27.7 | 0.7 |
| Nitrophenols | kg/h | | | | | | | | | |
| Water | kg/h | 1,338.7 | 34,041.4 | 1,900.0 | 6,766.8 | 30.7 | 7,101.6 | 7,101.6 | 5,166.5 | 1,935.1 |
| Sulfuric Acid | kg/h | | | | | | | | | |
| Nitric Acid | kg/h | | | | | | | | | |
| Sodium Hydroxide | kg/h | | | | | | | | | |
| Sodium Sulfate | kg/h | | 131.3 | | | | | | | |
| Ammonia | kg/h | | 2.8 | | | 13.2 | 57.7 | 57.7 | 56.5 | 1.2 |
| Ammonium Nitrophenolates | kg/h | | 2.0 | | | | 108.1 | 108.1 | 2.0 | 106.1 |
| Ammonium Bicarbonate | kg/h | | 21.2 | | | | | | | |
| Oxygen | kg/h | | | | | | | | | |

TABLE 4-continued

Stream Table for FIG. 4 (Invention with ammonia-based MNB washing plant and ammonia concentration)

| | | | | | | | | | | | |
|---|---|---|---|---|---|---|---|---|---|---|---|
| Nitrogen | kg/h | | | | | | | | | | |
| Carbon Dioxide | kg/h | | | | | | | | | | |
| Stream Number | | 118 | 119 | 120 | 121 | 122 | 123 | 124 | 125 | 126 | 127 |
| Total Flow | kg/h | 5,400.0 | 2,043.2 | 106.4 | 1,971.1 | 178.4 | 290.0 | 4,868.6 | 384.1 | 800.0 | 384.1 |
| Benzene | kg/h | | | | | | | | | | |
| Mononitrobenzene | kg/h | | 0.7 | | | | | 1.4 | 26.3 | | 26.3 |
| Nitrophenols | kg/h | | | | | | | | | | |
| Water | kg/h | 5,400.0 | 1,935.1 | | 1,949.9 | 8.6 | 290.0 | 4,862.4 | 304.1 | 800.0 | 304.1 |
| Sulfuric Acid | kg/h | | | | | | | | | | |
| Nitric Acid | kg/h | | | | | | | | | | |
| Sodium Hydroxide | kg/h | | | | | | | | | | |
| Sodium Sulfate | kg/h | | | | | | | | | | |
| Ammonia | kg/h | | 1.2 | | | | | 2.8 | 53.7 | | 53.7 |
| Ammonium Nitrophenolates | kg/h | | 106.1 | | | | | 2.0 | | | |
| Ammonium Bicarbonate | kg/h | | | | 21.2 | | | | | | |
| Oxygen | kg/h | | | 106.4 | | 21.3 | | | | | |
| Nitrogen | kg/h | | | | | 19.5 | | | | | |
| Carbon Dioxide | kg/h | | | | | 129.1 | | | | | |

DETAILED DESCRIPTION OF PREFERRED EMBODIMENT

The features and details of the integrated process of the present invention will now be described with reference to the attached figures. Three examples of the invention used in mononitrobenzene (MNB) manufacture are given. Example 1 uses sodium hydroxide as the alkali source in washing. Examples 2 and 3 use an ammonia solution in washing. The same letter in the different figures represents the same process unit operation. The stream numbers given on the figures refer to Tables 1–1 containing stream compositions and flows. Examples 4–7 are set forth to illustrate supercritical water oxidation of an ammonium dinitrophenolate stream, representative of redwater from an ammonia-based MNB washing system.

The principal features of the invention can be employed in various embodiments, including adiabatic or isothermal nitrations of benzene, toluene and xylene, without departing from the scope of the invention.

FIG. 1 illustrates the processing stages typical of nitroaromatic manufacture. Flow rates and compositions of the various streams for the case of a 50 metric ton per hour MNB plant are shown in Table 1 and are representative of actual plant operating conditions, although conditions vary from plant to plant. The invention integrates the treatment of nitro-hydroxy-aromatic effluent, commonly called strong effluent or red water, with acidic extraction or washing (stage C), alkaline washing (stage D) and weak effluent stripping/neutralization (stage G).

With reference to MNB manufacture, crude MNB is produced in a nitration stage (A) by nitrating benzene in a mixture of nitric acid and sulfuric acid. Commonly the spent sulfuric acid (stream 9) is concentrated back to process strength (B) and recycled back (stream 10) to the nitration stage. The sulfuric acid concentration step can be thermally integrated into the nitration step, as in the case of the adiabatic processes (U.S. Pat. Nos. 4,021,498, 4,091,042, 5,313,009, and 5,763,697). In the case of isothermal nitration, the spent sulfuric acid is brought back to strength in a separate acid concentration plant.

MNB condensate (stream 12) from acid concentration (B) is recovered and routed to washing. Aqueous condensate (stream 16) from acid concentration (B) is typically routed to effluent stripping and neutralization (F).

The crude MNB from nitration (stream 11) is contacted with water to remove mineral acids, principally sulfuric and nitric acids, in an acidic washing stage (C). Either fresh or process generated water can be used. If the wash water is maintained sufficiently acidic, the great majority of the nitrophenols will remain in the organic phase, leaving the acidic wash water (stream 17) with low levels of nitrophenols. The acidic wash water is typically combined with other low-nitrophenol water (F) and steam stripped to remove and recover benzene and MNB (G). The stripped effluent, often called weak effluent because of the low concentration of nitrophenols, is normally neutralized and discharged to a biological treatment process or to receiving waters.

From the acidic washing stage (C), crude MNB (stream 13), which now has the bulk of the mineral acids removed, is sent to a multistage, counter-current alkaline wash stage (D). Under alkaline conditions, nitrophenols in the crude MNB are extracted into the aqueous phase. The washed organic (stream 14) is then stripped of excess benzene (E) to produce product MNB (stream 15).

As treatment of nitrophenol water is costly, water make-up (stream 6) to the alkaline wash stage (D) may be minimized in order to reduce the strong effluent (stream 25) treatment costs (H). Fresh or process generated water may be used as make-up to alkaline washing. The alkali source (stream 5) in alkaline washing is commonly sodium hydroxide. Ammonia solution is also used in alkaline washing instead of sodium hydroxide where the strong effluent is incinerated as no ash is produced from combustion. Since ammonia is a weaker base compared with sodium hydroxide, ammonia washing systems typically exhibit reduced nitrophenol extraction stage efficiency.

EXAMPLE 1

Caustic Soda Based MNB Washing

FIG. 2 shows an example of the present invention integrated with a MNB plant using sodium hydroxide as the base in alkaline washing. Crude MNB (stream 30) from nitration (A) is processed through an acidic extraction or washing stage (C), alkaline washing (D) and subsequently passed to benzene stripping (stream 32).

The acidic wash stage (C) is an important feature of the presently disclosed integrated process as it removes sulfuric acid from the crude MNB. If sulfuric acid were to reach alkaline washing (D), the strong effluent would contain sulfate, a compound that will form a scale under supercritical water oxidation conditions.

Strong effluent (stream 44) from alkaline washing (D) is sent to storage (H) and then to an effluent concentrator (I) (stream 45) where the nitrophenol concentration in the effluent is raised from about 2% by weight to about 6 to 8% by weight. Nitrophenol concentrations in industrial washing systems are typically maintained below 1 to 2% to maintain acceptable washing efficiency. A simple atmospheric evaporator using low or medium pressure steam is preferred. The concentrate (stream 47) flows to storage (J) and subsequently (stream 49) to supercritical water oxidation (K). To ease handling and safety concerns, it is desirable that the nitrophenol concentrations are below the solubility limits, but slurries could also be handled with the current invention. Shown below in Table 5 are experimentally determined solubility data at 100° C. for sodium and ammonium 2,4-dinitrophenolate at 100° C. 2,4-Dinitrophenol is the most prevalent nitrophenol compound produced during conventional adiabatic MNB manufacture.

TABLE 5

Experimentally determined sodium and ammonium dinitrophenol at 100° C.

| | Sodium 2,4-Dinitrophenolate at pH 11 | Ammonium 2,4-Dinitrophenolate with 0.5% excess $NH_3$ |
|---|---|---|
| Solubility expressed as dinitrophenol (wt %) at 100° C. | 6.9 | 5.2 |

The concentrator overheads (stream 46) contain water, MNB and traces of nitrophenols. In the example provided, 75% of the feed water is evaporated, condensed and recycled back to alkaline washing. As the vapor pressure of nitrophenols in alkaline solution is very low, only trace amounts of nitrophenols are taken overhead in the effluent concentrator. Due to this recycle of relatively clean water, fresh water make-up to alkaline washing can be significantly reduced. Water make-up to industrial nitrobenzene alkaline washing systems is typically 0.15–0.25 kg per kg of nitrobenzene. Wash water make-up to alkaline washing is often demineralized or other high purity water. Recycle of the effluent concentrator overheads reduces the wash water input to 0.04–0.06 kg per kg of nitrobenzene, and correspondingly reduces the total aqueous effluent discharge by the same amount.

Nitrobenzene solubility in water is temperature dependent and ranges from about 0.2% to 0.5% for conditions present in industrial nitrobenzene washing systems. The bulk of soluble nitrobenzene in the strong effluent (stream 44) is stripped overhead in the effluent concentrator (I) and recycled back to alkaline washing, thus recovering valuable product.

In addition to recovery of water and nitrobenzene, effluent concentration facilitates subsequent supercritical water oxidation treatment. Firstly, it reduces the volume of the effluent, reducing equipment size and cost. Secondly, an effluent containing from 6–10% nitrophenol has a sufficient higher heating value of 1400 to 1850 kJ/kg of solution to allow self-sustaining (autogenous) operation of the supercritical water oxidation unit, while allowing energy to be recovered as medium pressure steam. Nitrophenol destruction under supercritical conditions is very high, over 99.99%. TOC reduction of 99.9% is also readily achievable. Supercritical water oxidation of nitrophenol effluent is described in Examples 4, 5, 6 and 7 below.

The strong effluent concentrator (I) shown in FIG. 2 is an atmospheric evaporator using steam as the heat source. Commercial hydrogenation processes of nitroaromatic compounds commonly produce significant excess quantities of low-pressure steam, which is suitable for use in effluent concentration, much of which is normally vented. Another possible concentration process is membrane separation, such as reverse osmosis.

The effluent concentrate (stream 49) is fed to the supercritical water oxidation unit (K). The feed stream in the presence of an oxygen source is exposed in the supercritical water oxidation unit to temperatures and pressures which are supercritical for water, typically 500 to 600° C. at 25 MPa, which result in a substantial portion of the nitrophenols and other organics being oxidized to carbon dioxide, water, nitrous oxide and nitrogen. organically bound sodium is released and, along with free sodium hydroxide in the strong effluent, reacts with carbon dioxide to form sodium carbonate. Due to the fouling nature of sodium carbonate in a supercritical water oxidation reactor, a special reactor configuration or cleaning system is used in order to prevent the reactor from plugging. Examples of suitable reactor configurations and cleaning systems for use in the present invention, which may be applied in combination, are described in U.S. Pat. Nos. 4,543,190, 4,338,199, 5,252,224, 4,543,057, 5,560,823, 5,620,606, 5,570,889, and 5,890,531, the teachings all of which are incorporated herein by reference. Gaseous and aqueous effluents are formed upon cooling. The gaseous effluent (stream 52) is rich in carbon dioxide and oxygen, and can likely be vented directly to atmosphere. Depending on the reactor configuration chosen, the sodium carbonate is either recovered with the aqueous effluent, with flushing water, or in a concentrated brine. For purposes of this example, the former configuration is assumed, which can be achieved by the combination of a tubular reactor and a cleaning system such as that described in U.S. Pat. No. 5,890,531.

The treated effluent (stream 51) contains sodium carbonate and very low levels of organics. The treated effluent can be discharged directly to receiving waters or a publicly owned treatment (POT) facility after pH adjustment. Alternatively, the alkali value of the treated effluent (stream 51) can be used to neutralize sulfuric acid present in the acidic wash water (stream 34), thus reducing alkali make-up (stream 38) to weak effluent neutralization (G). Thus, one surprising result of this invention is that the alkali value in the caustic soda fed to alkaline washing is utilized twice; firstly to neutralize nitrophenol and secondly to neutralize sulfuric acid, as it is effectively regenerated by the supercritical water oxidation treatment.

EXAMPLE 2

Ammonia Based MNB Washing

FIG. 3 illustrates a second example of the present invention integrated with a MNB plant. The process is essentially the same as that described in Example 1, with the exception that aqueous ammonia is used as the alkali source for washing. Ammonia is generally used where the spent alkaline wash water (strong effluent) is incinerated. In contrast to caustic soda, ammonia and the resulting ammonium salts produce no ash upon incineration, or other forms of oxidation.

There are a number of notable differences between caustic and ammonia washing:

1. Ammonia is a weaker base than caustic and thus ammonia based washing systems generally have lower nitro-hydroxy-aromatic extraction efficiencies. In MNB manufacture, extraction of mononitrophenol in ammonia washing is especially poor compared to caustic based washing.

2. Greater molar excess of ammonia is required than caustic for efficient nitro-hydroxy-aromatic extraction. Spent ammonia wash water may have from 0.2 to 1% free $NH_3$. As this free ammonia is generally lost through incineration, ammonia consumption in washing is significantly higher than caustic on a molar basis.

3. Ammonium nitro-hydroxy-aromatic salts generally have lower aqueous solubility compared to sodium based salts. This often requires that the alkaline washers using ammonia run warm (50–80° C.) to maintain nitro-hydroxy-aromatic salt solubility. For example, in conducted experimental tests, the solubility of ammonium 2,4-dinitrophenolate in water at 100° C. was determined to be 5.2% as dinitrophenol, while the solubility of sodium 2,4-dinitrophenolate at 100° C. was determined to be 6.9% as dinitrophenol (see Table 5).

4. Ammonia has a significant vapor pressure, which permits recovery of excess ammonia from effluent streams.

As noted previously, the process unit operations for the ammonia-based washing example (FIG. 3) are essentially identical to the caustic-based example (FIG. 2). However, there are a number of significant, non-obvious differences between the invention with ammonia-based washing system and with caustic-based washing, which are described below.

The primary role of the strong effluent concentrator (I) is to reduce the throughput and cost of supercritical water oxidation (K). Surprisingly, the concentration of ammonia wash waters also provides a number of additional benefits. The bulk of the free ammonia in the strong effluent is stripped in the strong effluent concentrator (I) and recycled back to the alkaline washers (D). In addition to recovering MNB and wash water, this reduces the fresh ammonia make-up (stream 71) to about the stoichiometric alkali demand of the nitrophenols. Recovery of excess ammonia can reduce overall ammonia consumption by 75% or higher.

Another important benefit of the recovery of excess ammonia in the strong effluent concentrator is that higher excess ammonia concentration may be used in the ammonia wash water without an increase in ammonia consumption. This is significant because nitro-hydroxy-aromatic extraction efficiency improves with increasing ammonia concentration in the wash water. For example, in conducted tests, extraction efficiency of 2-nitrophenol from crude MNB was found to increase by 50% when the free ammonia concentration in wash water was increased from 0.2% to 1%. Thus, operation with higher free ammonia concentrations significantly improves MNB product quality by reducing residual nitrophenols.

Yet another benefit of recovery of excess ammonia in the strong effluent concentrator is that the total ammonia concentration in the feed to supercritical water oxidation is greatly reduced. From supercritical water oxidation tests with ammonia redwater, it has been found that approximately 50% of the ammonia is converted to nitrogen, nitrous oxide and water. The remaining ammonia combines upon cooling with carbon dioxide and water to form ammonium bicarbonate in the aqueous effluent. The bicarbonate in the effluent buffers the pH to typically about 7 to 8. Reducing the ammonia level in the feed to supercritical water oxidation has at least two advantages: reduced oxygen consumption and reduced residual ammonium concentration in the final effluent.

In this example, due to the volatile nature of ammonia and ammonium salts, special supercritical reactor designs or reactor cleaning methods are not required to cope with fouling, since the there are no significant levels of fouling compounds in the feed.

EXAMPLE 3

Ammonia Based MNB Washing with Ammonia Concentration

In the manufacture of MNB, following washing, benzene is stripped from the crude MNB. If a live steam stripper is used, a significant amount of aqueous condensate is produced that can contain low levels of nitrophenols, in some cases at greater levels than can be tolerated in the weak effluent system. In this case, it is convenient to use the stripper condensate as make-up water to the alkaline washers. The ratio of stripper condensate to crude MNB typically ranges from about 0.05 to 0.09 kg/kg, much higher than the fresh water make-up rate shown in Examples 2 and 3.

As in example 2, FIG. 4 illustrates the present invention integrated with a MNB plant which utilizes ammonia in alkaline washing. However, ammonia distillation (L) has been added to the overheads from the strong effluent concentrator (I). In recovering a relatively concentrated ammonia solution, for example 10 to 15% by weight ammonia, a larger water make-up is allowed to the alkaline washers. This permits disposal of nitrophenol containing process water, such as the stripper condensate mentioned above, in the alkaline washers.

In Table 4, the overheads (stream 116) from the strong effluent concentrator (I) are shown to contain about 1% ammonia. This stream can be concentrated in an atmospheric distillation column to 10 to 15% using an indirect reboiler and a reflux condenser. The rich ammonia solution (stream 125) is then recycled back to alkaline washing (D). The ammonia stripper bottoms (stream 124) contains traces of ammonia, MNB and nitrophenols. This stream can be processed through the weak effluent stripper The methods described above in examples 2 and 3 can be equally applied when the final treatment step for the concentrated nitro-hydroxy-aromatic effluent is replaced by incineration—also known as thermal oxidation—or by an aqueous phase thermal treatment processes. Examples of such aqueous phase processes include: wet air oxidation, wherein the treatment pressure and temperature, in the presence of air or oxygen, are sub-critical for water; the processes of Baur et al (U.S. Pat. No. 5,232,605) and Carr et al (U.S. Pat. No. 5,762,802), wherein nitric acid is used to digest and oxidize the nitro-hydroxy-aromatic compounds in pressurized thermal treatment; the process of Sawicki et al (U.S. Pat. No. 5,250,193), wherein thermal oxidation is carried out at a pressure supercritical for water, but at a temperature sub-critical for water; and the process of Larbig et al (U.S. Pat. No. 4,230,567), wherein the thermal degradation is carried out under pressures and temperatures sub-critical for water, without the addition of an oxygen scurce. These methods, although they are not as advantageous as treatment by supercritical water oxidation, preserve many of the novel features of the integrated process described above such as recovery of water and chemicals; lower treatment plant costs due to reduction of the volume of effluent by the concentration stage; and reduced energy costs for heating, or evaporating and heating, the nitrohydroxy-aromatic aqueous effluent to treatment temperatures.

EXAMPLE 4

Figure 5:
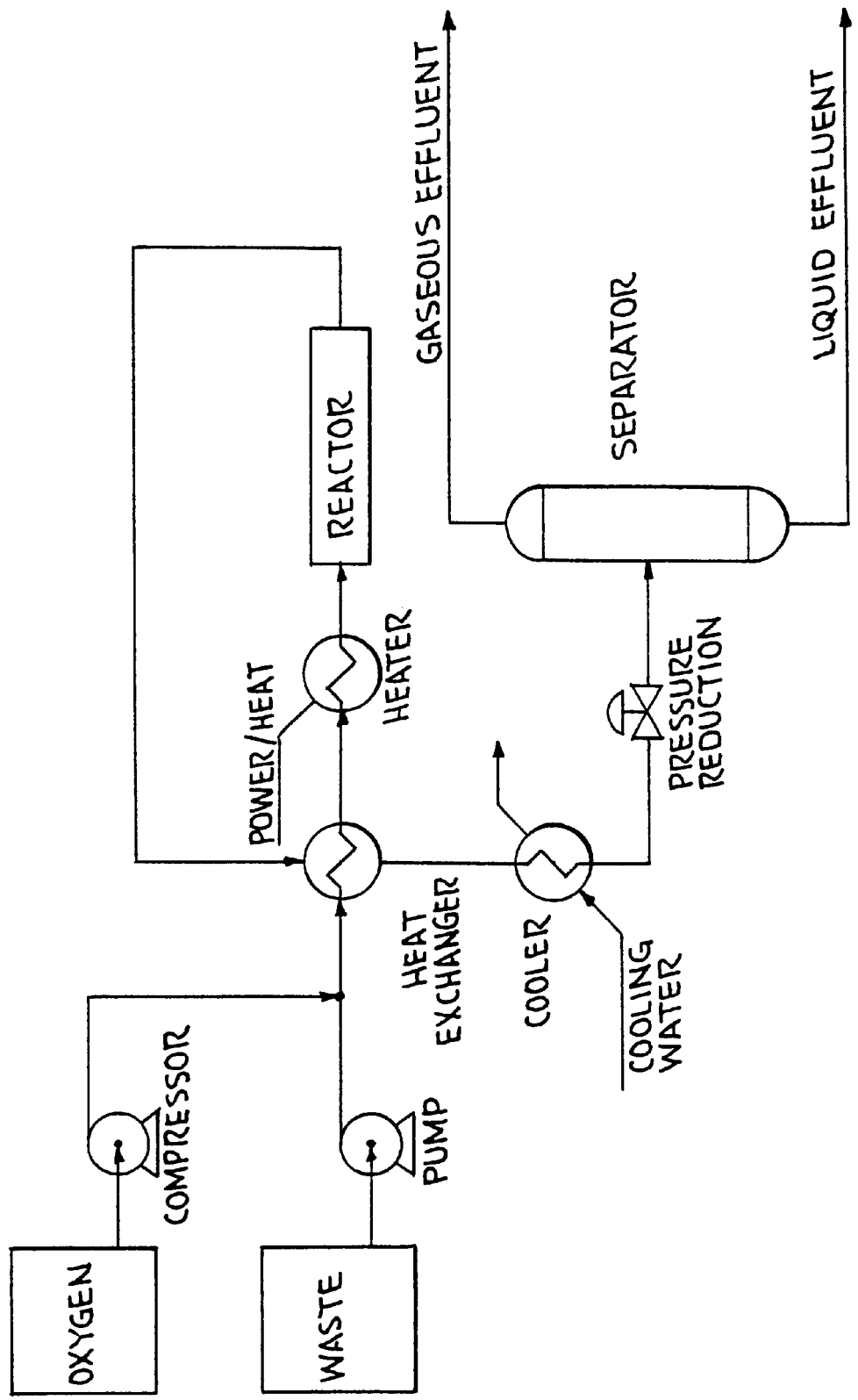
FIG. 5 is a schematic representation of the supercritical water oxidation pilot plant employed in following Examples 4, 5, 6 and 7.

Supercritical Water Oxidation Treatment of Ammonium 2,4 Dinitrophenolate Solution In this example, a synthetic solution containing 1.12 wt % 2,4-dinitrophenol and about 0.5 wt % free ammonia in water was treated at about 25 MPa and 600° C., with feed flow rate of 0.26 liters per minute and an oxygen flow rate of 1.30 kg/h. This effluent is representative of unconcentrated MNB redwater from an ammonia-based washing system. The test was performed in a pilot plant with a tubular reactor as depicted in FIG. 5. The residence time in the reactor was about 70 seconds. Feed and aqueous effluent analysis results are summarized in Table 6. Carbon monoxide was not detected in the vent gas. Both TOC and dinitrophenol are below detection limits in the effluent.

EXAMPLE 5

Supercritical Water Oxidation Treatment of Ammonium 2,4 Dinitrophenolate Solution In this example the same solution as in example 4 was treated at about 25 MPa and 500° C. with a feed flow rate of 0.61 liters per minute and an oxygen flow rate of 1.17 kg/h. The residence time in the reactor was about 30 seconds. Feed and aqueous effluent analysis results are summarized in Table 6. No simultaneous gas analysis was taken. Again, both TOC and dinitrophenol are below detection limits in the effluent.

EXAMPLE 6

Supercritical Water Oxidation Treatment of Ammonium 2,4 Dinitrophenolate Solution In this example, the same solution as in examples 4 and 5 was treated at about 25 MPa and 600° C. with a feed flow rate of 1.33 liters per minute and an oxygen flow rate of 6.08 kg/h. The residence time in the reactor was about 10 seconds. Feed and aqueous effluent analysis results are summarized in Table 6. Carbon monoxide was not detected in the gaseous effluent. Again, both TOC and dinitrophenol are below detection limits in the effluent.

TABLE 6

Feed and effluent analysis of ammonia redwater supercritical water oxidation tests

| Test | Variable | Feed (ppm) | Effluent (ppm) |
|---|---|---|---|
| Example #4 | TOC | 4,328[1] | <5[4] |
|  | 2,4-Dinitrophenol | 11,056[2] | <1[4] |
|  | $NH_3$ as Nitrogen[5] | 4,735 | 2,164 |
|  | pH | 10.2 | 7.5 |
|  | Nitrate | 1.6 | 0.13 |
|  | Nitrite | n.d. | n.d. |
|  | Bicarbonate | n.a. | 8,128[3] |
| Example #5 | TOC | 4,328[1] | <5[4] |
|  | 2,4-Dinitrophenol | 11,056[2] | <1[4] |
|  | $NH_3$ as Nitrogen[5] | 4,735 | 2,858 |
|  | pH | 10.2 | 7.5 |
|  | Nitrate | 1.6 | 0.46 |
|  | Nitrite | n.d. | n.d. |
|  | Bicarbonate | n.a. | 10,998[3] |

TABLE 6-continued

Feed and effluent analysis of ammonia redwater supercritical water oxidation tests

| Test | Variable | Feed (ppm) | Effluent (ppm) |
|---|---|---|---|
| Example #6 | TOC | 4,328[1] | <5[4] |
|  | 2,4-Dinitrophenol | 11,056[2] | <0.5 |
|  | $NH_3$ as Nitrogen[5] | 4,483 | 2,101 |
|  | pH | 8.9 | 8.0 |
|  | Nitrate | <0.25[4] | 0.4 |
|  | Nitrite | n.d. | n.d. |
|  | Bicarbonate | n.a. | 9,246[3] |

[1]Calculated from dintrophenol analysis
[2]Average of 3 analyses, 11051, 11188, 10930 ppm
[3]Calculated from inorganic carbon, assuming all present as bicarbonate
[4]Less than the detection limit at the analysis dilution ratio
[5]Includes ammonia and ammonium
n.d. = none detected - flat baseline on chromatograph
n.a. = not analyzed

EXAMPLE 7

Supercritical Water Oxidation Treatment of Ammonium 2,4 Dinitrophenolate Solution In this example, a solution of 1.40% 2,4-dinitrophenol and about 1.1% free ammonia in water was treated at about 25 MPa with a feed flow rate of 1.0 liters per minute and an oxygen flow rate of 2.5 kg/h. Due to heat losses, the reactor temperature varied from about 600° C. at the inlet to about 470° C. at the outlet. In this test, particular attention was paid to the analysis of nitrogen compounds in the aqueous and gaseous effluents. The analysis results are presented in Table 7 and demonstrate that even without complete destruction of dinitrophenol, no measurable amount of NOx gases is formed and that ammonia content in the vent gas is very low. The low nitrate and non-detectable nitrite levels in examples 4 through 7 further demonstrate that NOx gas formation and subsequent nitrate formation are not evident to any appreciable extent in the supercritical water oxidation treatment of either dinitrophenolate or of ammonia.

TABLE 7

Distribution of nitrogen species after supercritical water oxidation treatment of 2,4 ammonium dinitrophenolate

| Test | Variable | Feed (ppm) | Effluent (ppm) |
|---|---|---|---|
| Example #7 | 2,4-Dinitrophenol | 14,000 | 9.8 |
|  | $NH_3$ as Nitrogen[1] | 10,406 | 3,491 |
|  | Nitrate | n.d. < 5 | n.d. (<5) |
|  | Nitrite | n.d. < 5 | n.d. (<5) |

| | | | Gaseous Effluent |
|---|---|---|---|
|  | Nitrogen |  | 25 v/v % |
|  | Nitrous Oxide |  | 3.6 v/v % |
|  | Ammonia |  | 3.55 ppmv |
|  | Nitrogen Oxides (NO and $NO_2$) |  | n.d. (<0.6 ppmv) |

[1]Includes ammonia and ammonium
n.d. - below the analytical detection limit at the analysis dilution ratio

EQUIVALENTS

Those skilled in the art will recognize, or be able to ascertain using no more than routine experimentation, many equivalents to the specific embodiments of the invention described herein. Such equivalents are intended to be encompassed in the following claims.

It is claimed:

1. A method of integrating nitroaromatic washing with supercritical water oxidation treatment of the effluent, comprising the steps of:
   (a) washing of the crude nitroaromatic product from a nitroaromatic synthesis process, whereby the synthesis occurs in a mixture of sulfuric and nitric acid, with acidic water to remove the majority of the mineral acids, followed by separation of the nitroaromatic from the acidic water;
   (b) washing of the nitroaromatic product from the acidic washing step in alkaline water to remove substantially all of the nitro-hydroxy-aromatic byproducts, followed by separation of the nitroaromatic from the aqueous effluent;
   (c) concentration of the aqueous effluent from the alkaline washing step by removal of water and volatile components to near or above the nitro-hydroxy-aromatic solubility;
   (d) recycle of water and volatile components removed in the effluent concentrator to the alkaline washing step to recover water and product;
   (e) treatment of the concentrated nitro-hydroxy-aromatic effluent in the presence of an oxygen source at conditions supercritical for water, to thereby oxidize a substantial portion of the nitro-hydroxy-aromatic and other organic compounds.

2. A method of claim 1, wherein sodium or potassium hydroxide is used as the base in the alkaline washing step, and the alkali value of the effluent from supercritical water oxidation treatment is used for neutralization of the effluent from the acidic washing step.

3. A method of claim 1, wherein ammonia is used as the base in alkaline washing and is recovered in the effluent concentration step and is recycled together with the water and volatile compounds to the alkaline washing step.

4. A method of claim 3, wherein 0.5 to 1.5% by weight free ammonia is present in the alkaline water used in the alkaline washing step.

5. A method of claim 3, wherein the recovered ammonia, water and nitroaromatic from the concentration step is further treated by distillation to produce a concentrated ammonia solution, which is recycled to alkaline washing, and a water stream, which is not recycled.

6. A method according to claim 1, 2, 3, 4 or 5, wherein the nitroaromatic is mononitrobenzene and the nitro-hydroxy-aromatic compounds are mono-, di- and tri-nitrophenols.

7. A method according to claim 1, 2, 3, 4 or 5, wherein the nitroaromatic is mono- or dinitrotoluene and the nitro-hydroxy-aromatic compounds are mono-, di- and tri-nitrocresols.

8. A method according to claim 1, 2, 3, 4 or 5, wherein the nitroaromatic is mononitroxylene and the nitro-hydroxy-aromatic compounds are mono-, di- and tri-nitroxylenols.

9. A method of claim 3 or 4, wherein step (e) of treatment of the concentrated nitro-hydroxy-aromatic effluent is incineration.

10. A method of claim 3 and 4, wherein step (e) of treatment of the concentrated nitro-hydroxy-aromatic effluent is thermal treatment in the aqueous phase.

11. A method of claim 1, wherein the concentration step is achieved by evaporation.

12. A method of claim 1, wherein the concentration step is achieved by membrane separation.

13. Process of producing nitroaromatics comprising the steps of:
   (a) contacting an aromatic with a nitrating solution of sulfuric acid and nitric acid to produce a nitroaromatic;
   (b) subjecting the nitroaromatic reaction product of (a) to an alkaline wash to provide a washed nitroaromatic product and an aqueous concentrate containing organic components, including nitro-hydroxy-aromatic by-products, mixed with said nitroaromatic, wherein the concentrate is prepared to a concentration of solubility of the nitro-hydroxy-aromatic by-products; and
   (c) subjecting the aqueous concentrate of (b) to supercritical water oxidation to oxidize said organic components.

14. Process of claim 13 wherein the reaction product of (a) is subjected to a wash with acidic water to remove mineral acids before performing the alkaline wash of step (b).

15. Process of claim 13 or 14 wherein said aromatic is benzene and said nitroaromatic is mononitroberzene.

16. The process of claim 13 or 14 wherein said aromatic is toluene and said nitroaromatic is a dinitrotoluene.

* * * * *

UNITED STATES PATENT AND TRADEMARK OFFICE
CERTIFICATE OF CORRECTION

PATENT NO. : 6,288,289 B1
DATED : September 11, 2001
INVENTOR(S) : David Anthony Boyd et al.

It is certified that error appears in the above-identified patent and that said Letters Patent is hereby corrected as shown below:

Column 8,
Table 3, Total Flow under Stream Number 79 should read -- 2,081.7 -- instead of "2,008.2".

Column 14,
Line 44, insert -- (G). -- after "stripper".
Line 63, "scurce" should read -- source --.

Column 18,
Line 42, "mononitroberzene" should read -- mononitrobenzene --.

Signed and Sealed this

Twenty-eighth Day of May, 2002

Attest:

JAMES E. ROGAN
Director of the United States Patent and Trademark Office

Attesting Officer